US006584975B1

(12) United States Patent
Taylor

(10) Patent No.: US 6,584,975 B1
(45) Date of Patent: Jul. 1, 2003

(54) RESPIRATOR MASK FOR FILTERING BREATHED AIR

(76) Inventor: Eldridge Taylor, 4401 5th Ave. #100, Lake Charles, LA (US) 70607

( * ) Notice: Subject to any disclaimer, the term of this patent is extended or adjusted under 35 U.S.C. 154(b) by 75 days.

(21) Appl. No.: 09/649,881

(22) Filed: Aug. 28, 2000

(51) Int. Cl.[7] ......................... A61M 16/00; A62B 18/08

(52) U.S. Cl. ............................. 128/206.11; 128/206.12; 128/206.13

(58) Field of Search ........................ 128/205.77, 205.29, 128/206.12, 206.13, 206.17, 206.21, 206.27, 206.28, 206.29, 207.11, 207.18, 206.11

(56) References Cited

U.S. PATENT DOCUMENTS

| | | | | | |
|---|---|---|---|---|---|
| 443,191 | A | * | 12/1890 | Illing | |
| 535,718 | A | * | 3/1895 | Nagler | |
| 1,050,621 | A | * | 1/1913 | De Ford | 128/206.28 |
| 1,175,799 | A | * | 3/1916 | Niessner | 128/206.11 |
| 1,362,766 | A | * | 12/1920 | McGargill | 128/205.27 |
| 3,020,911 | A | * | 2/1962 | Girden | 128/141 |
| 4,029,092 | A | * | 6/1977 | Morgan | 128/201.11 |
| 4,470,413 | A | * | 9/1984 | Warncke | 128/201.18 |
| 4,549,543 | A | * | 10/1985 | Moon | 128/206.12 |
| 4,890,609 | A | * | 1/1990 | Wilson, II | 128/206.28 |
| 5,086,768 | A | * | 2/1992 | Niemeyer | 128/205.24 |
| 5,375,593 | A | * | 12/1994 | Press | 128/207.18 |
| 5,603,317 | A | * | 2/1997 | Farmer | 128/205.27 |
| 6,298,849 | B1 | * | 10/2001 | Scholey et al. | 128/205.27 |

* cited by examiner

*Primary Examiner*—Weilun Lo
*Assistant Examiner*—Mital Patel
(74) *Attorney, Agent, or Firm*—Goldstein & Lavas, P.C.

(57) ABSTRACT

A respirator mask for filtering breathed air including a mask portion dimensioned for covering the mouth of the user. The mask portion includes an inner portion, an outer portion, and an air chamber therebetween. The mask portion includes a generally circular peripheral edge. The peripheral edge includes a top edge, a bottom edge, and opposed side edges. The mask portion includes a recessed mouth section on the inner portion thereof. The recessed mouth section includes a central aperture in communication with the air chamber. The mask portion includes a pair of air vents secured to the outer portion thereof. The pair of air vents each have open inner and outer ends. The open inner ends are in communication with the air chamber. A mouthpiece portion is removably coupled with respect to the mask portion. The mouthpiece portion includes a shield portion dimensioned for positioning within the recessed mouth section of the mask portion. The shield portion includes a central opening that is alignable with the central aperture of the recessed mouth section. The mouthpiece portion includes an inner tube having an open inner end and an open outer end. The open outer end is secured to the central aperture of the shield portion. The open inner end is positionable within the user's mouth.

7 Claims, 2 Drawing Sheets

RESPIRATOR MASK FOR FILTERING BREATHED AIR

BACKGROUND OF THE INVENTION

The present invention relates to a respirator mask for filtering breathed air and more particularly pertains to preventing a user from breathing unfiltered air.

The use of respirator devices is known in the prior art. More specifically, respirator devices heretofore devised and utilized for the purpose of absorbing fumes and the like are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,964,900 to Thompson discloses et al. discloses a respirator filter means for the removal of tritiated water comprising fluid inlet and output ports. U.S. Pat. No. 4,967,742 to Theodorou discloses a portable breathing device. U.S. Pat. No. 4,754,751 to Mausteller et al. discloses an escape respirator having a mouthpiece that is directly connected to a chemical canister. U.S. Pat. No. 5,720,279 to Furuichi et al. discloses a semi-closed respirator used in diving.

While these devices fulfill their respective, particular objective and requirements, the aforementioned patents do not describe a respirator mask for filtering breathed air for preventing a user from breathing unfiltered air.

In this respect, the respirator mask for filtering breathed air according to the present invention substantially departs from the conventional concepts and designs of the prior art, and in doing so provides an apparatus primarily developed for the purpose of preventing a user from breathing unfiltered air.

Therefore, it can be appreciated that there exists a continuing need for a new and improved respirator mask for filtering breathed air which can be used for preventing a user from breathing unfiltered air. In this regard, the present invention substantially fulfills this need.

SUMMARY OF THE INVENTION

In the view of the foregoing disadvantages inherent in the known types of respirator devices now present in the prior art, the present invention provides an improved respirator mask for filtering breathed air. As such, the general purpose of the present invention, which will be described subsequently in greater detail, is to provide a new and improved respirator mask for filtering breathed air which has all the advantages of the prior art and none of the disadvantages.

To attain this, the present invention essentially comprises a mask portion dimensioned for covering the mouth of the user. The mask portion includes an inner portion, an outer portion, and an air chamber therebetween. The mask portion includes a generally circular peripheral edge. The peripheral edge includes a top edge, a bottom edge, and opposed side edges. The mask portion includes an elastic band having opposed ends secured to the opposed side edges thereof for extending around the user's head when the mask portion is positioned on the mouth of the user. The mask portion includes a pair of nose sections extending upwardly from the top edge thereof. The pair of nose sections each include upper ends positionable within the nose of the user. The pair of nose sections each have an air tube positioned therein. The air tubes have open upper and lower ends. The open upper ends are exposed through the upper ends of the nose sections. The open lower ends are in communication with the air chamber. The mask portion includes a recessed mouth section on the inner portion thereof. The recessed mouth section includes a central aperture in communication with the air chamber. The recessed mouth section includes a plurality of peripherally disposed protrusions extending inwardly therefrom. The mask portion includes a pair of air vents secured to the outer portion thereof. The pair of air vents each have open inner and outer ends. The open inner ends are in communication with the air chamber. The open outer ends each have a filter screen disposed therein. A mouthpiece portion is removably coupled with respect to the mask portion. The mouthpiece portion includes a shield portion dimensioned for positioning within the recessed mouth section of the mask portion. The shield portion includes a central opening that is alignable with the central aperture of the recessed mouth section. The shield portion includes a plurality of peripherally disposed apertures therethrough for selectively snap-engaging the peripherally disposed protrusions of the recessed mouth section. The mouthpiece portion includes an inner tube having an open inner end and an open outer end. The open outer end is secured to the central aperture of the shield portion. The open inner end has a peripheral flange. The open inner end is positionable within the user's mouth.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved respirator mask for filtering breathed air which has all the advantages of the prior art respirator devices and none of the disadvantages.

It is another object of the present invention to provide a new and improved respirator mask for filtering breathed air which may be easily and efficiently manufactured and marketed.

It is a further object of the present invention to provide a new and improved respirator mask for filtering breathed air which is of durable and reliable construction.

An even further object of the present invention is to provide a new and improved respirator mask for filtering breathed air which is susceptible of a low cost of manufacture with regard to both materials and labor, and which accordingly is then susceptible of low prices of sale to the consuming public, thereby making such a respirator mask for filtering breathed air economically available to the buying public.

Even still another object of the present invention is to provide a new and improved respirator mask for filtering breathed air for preventing a user from breathing unfiltered air.

Lastly, it is an object of the present invention to provide a new and improved respirator mask for filtering breathed air including a mask portion dimensioned for covering the mouth of the user. The mask portion includes an inner portion, an outer portion, and an air chamber therebetween. The mask portion includes a generally circular peripheral edge. The peripheral edge includes a top edge, a bottom edge, and opposed side edges. The mask portion includes a recessed mouth section on the inner portion thereof. The recessed mouth section includes a central aperture in communication with the air chamber. The mask portion includes a pair of air vents secured to the outer portion thereof. The pair of air vents each have open inner and outer ends. The open inner ends are in communication with the air chamber. A mouthpiece portion is removably coupled with respect to the mask portion. The mouthpiece portion includes a shield portion dimensioned for positioning within the recessed mouth section of the mask portion. The shield portion includes a central opening that is alignable with the central aperture of the recessed mouth section. The mouthpiece portion includes an inner tube having an open inner end and an open outer end. The open outer end is secured to the central aperture of the shield portion. The open inner end is positionable within the user's mouth.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
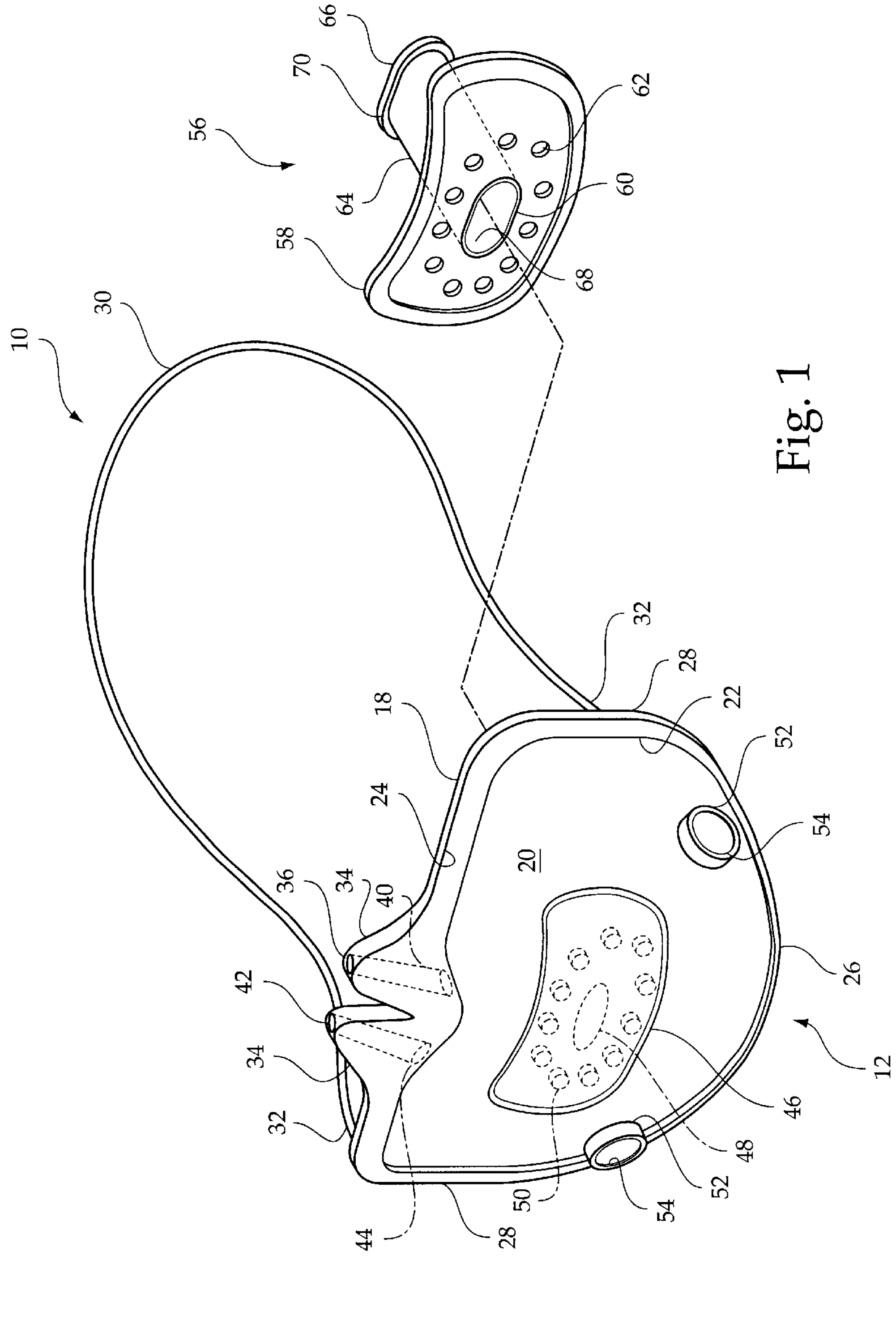
FIG. 1 is an exploded perspective view of the preferred embodiment of the respirator mask for filtering breathed air constructed in accordance with the principles of the present invention.
Figure 3:
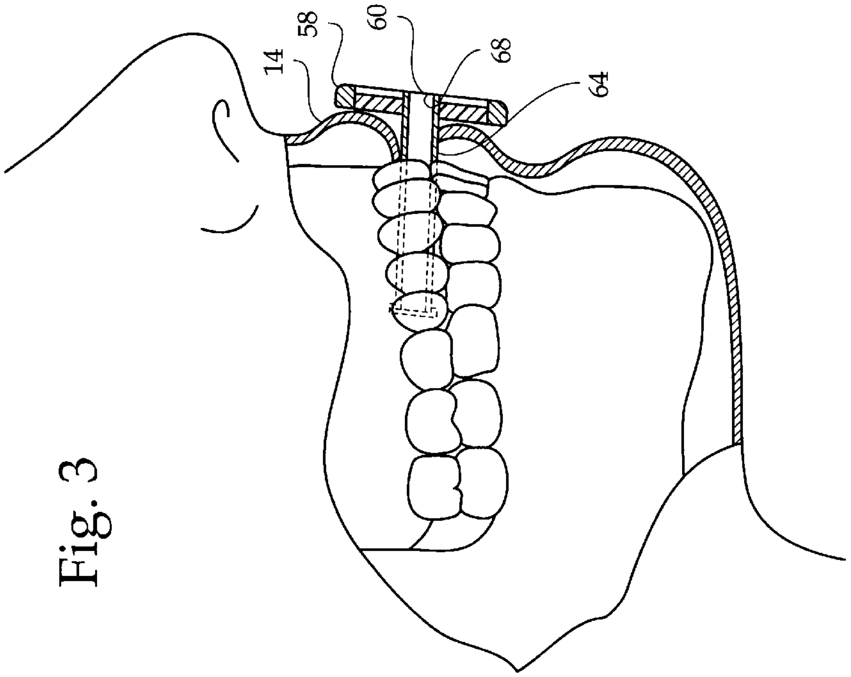
FIG. 3 is a cross-sectional side view of the mouthpiece illustrated in use.
Figure 2:
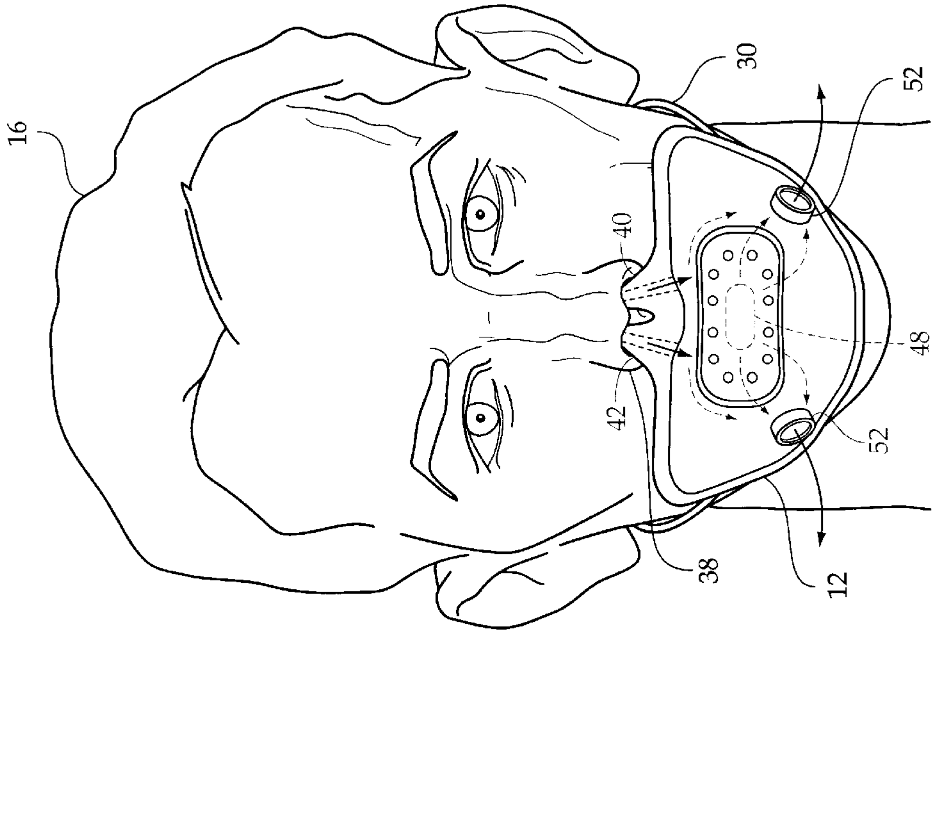
FIG. 2 is a front view of the present invention illustrated in use.

With reference now to the drawings, and in particular, to FIGS. 1 through 3 thereof, the preferred embodiment of the new and improved respirator mask for filtering breathed air embodying the principles and concepts of the present invention and generally designated by the reference number 10 will be described.

Specifically, it will be noted in the various figures that the device relates to a respirator mask for filtering breathed air for preventing a user from breathing unfiltered air. In its broadest context, the device consists of a mask portion and a mouthpiece portion. Such components are individually configured and correlated with respect to each other so as to attain the desired objective.

The mask portion 12 is dimensioned for covering the mouth 14 of the user 16. The mask portion 12 includes an inner portion 18, an outer portion 20, and an air chamber 22 therebetween. The mask portion 12 includes a generally circular peripheral edge. The peripheral edge includes a top edge 24, a bottom edge 26, and opposed side edges 28. The mask portion 12 includes an elastic band 30 having opposed ends 32 secured to the opposed side edges 28 thereof for extending around the user's head when the mask portion 12 is positioned on the mouth 14 of the user 16. An alternate type of band or adjustable strap could also be used to secure the mask portion 12 to the user's mouth. The mask portion 12 includes a pair of nose sections 34 extending upwardly from the top edge 24 thereof. The nose sections 34 are preferably "constructed of a soft, leather-like material to provide comfort to the user's nose. The pair of nose sections 34 each include upper ends 36 positionable within the nose 38 of the user 16. Note FIG. 2. The upper ends 36 will be comfortably positioned within the nostrils of the nose 38. The pair of nose sections 34 each have an air tube 40 positioned therein. The air tubes 40 have open upper and lower ends 42,44. The open upper ends 42 are exposed through the upper ends 36 of the nose sections 34. The open lower ends 44 are in communication with the air chamber 22. The mask portion 12 includes a recessed mouth section 46 on the inner portion 18 thereof. The recessed mouth section 46 includes a central aperture 48 in communication with the air chamber 22. The recessed mouth section 46 includes a plurality of peripherally disposed protrusions 50 extending inwardly therefrom. The mask portion 12 includes a pair of air vents 52 secured to the outer portion 20 thereof. The pair of air vents 52 each have open inner and outer ends. The open inner ends are in communication with the air chamber 22. The open outer ends each have a filter screen 54 disposed therein."

The mouthpiece portion 56 is removably coupled with respect to the mask portion 12. The mouthpiece portion 56 includes a shield portion 58 dimensioned for positioning within the recessed mouth section 46 of the mask portion 12. The shield portion 58 includes a central opening 60 that is alignable with the central aperture 48 of the recessed mouth section 46. The shield portion 58 includes a plurality of peripherally disposed apertures 62 therethrough for selectively snap-engaging the peripherally disposed protrusions 50 of the recessed mouth section 46. The mouthpiece portion 56 includes an inner tube 64 having an open inner end 66 and an open outer end 68. The open outer end 68 is secured to the central aperture 60 of the shield portion 58. The open inner end 66 has a peripheral flange 70. The open inner end 66 is positionable within the user's mouth 16. Note FIG. 3.

In use, the mouthpiece portion 56 is secured to the mask portion 12. The inner tube 64 is positioned within the mouth 16 as the mask portion 12 is positioned over the mouth 16 with the elastic band 30 positioned around the head. The device 10 allows for the flow of air in and out of the pair of air vents 52. The user can breath air via their nose through the air tubes 40 which will draw air through the air vents 52 and the inner chamber 22. The user can breath through the mouth 16 by sucking in air through the inner tube 64 which will also draw air through the air vents 52 into the inner chamber 22. The mouthpiece portion 56 can be easily removed from the mask portion 12 to allow another user to add their own mouthpiece portion 56 to the mask portion 12. Essentially, the device 10 operates as a changeable respirator with a personal mouthpiece. The mouthpiece portion 56 snaps into the mask portion 12 to filter various liquid particles, dust, and fumes. The device 10 is interchangeable for many types of work and can be used by multiple users simply by changing the mouthpiece portion 56.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letter Patent of the United States is as follows:

1. A respirator mask for filtering breathed air for preventing a user from breathing unfiltered air, wherein the user having a face including a mouth and nose, the respirator mask comprising, in combination:

a mask portion dimensioned for covering the mouth of the user, the mask portion including an inner portion, an outer portion, and an air chamber therebetween, the mask portion including a generally circular peripheral edge, the peripheral edge including a top edge, a bottom edge, and opposed side edges, the mask portion including an elastic band having opposed ends secured to the opposed side edges thereof for extending around the user's head when the mask portion is positioned on the mouth of the user, the mask portion including a pair of nose sections extending upwardly from the top edge thereof, the pair of nose sections each including upper ends positionable within the nose of the user, the pair of nose sections each having an air tube positioned therein, the air tubes having open upper and lower ends, the open upper ends being exposed through the upper ends of the nose sections, the open lower ends being in communication with the air chamber, the mask portion including a recessed mouth section on the inner portion thereof, the recessed mouth section including a central aperture in communication with the air chamber, the recessed mouth section including a plurality of peripherally disposed protrusions extending inwardly therefrom, the mask portion including a pair of air vents secured to the outer portion thereof, the pair of air vents each having open inner and outer ends, the open inner ends being in communication with the air chamber, the open outer ends each having a filter screen disposed therein; and a mouthpiece portion removably coupled with respect to the mask portion, the mouthpiece portion including a shield portion dimensioned for positioning within the recessed mouth section of the mask portion, the shield portion including a central opening being alignable with the central aperture of the recessed mouth section, the shield portion including a plurality of peripherally disposed apertures therethrough for selectively snap-engaging the peripherally disposed protrusions of the recessed mouth section, the mouthpiece portion including an inner tube having an open inner end and an open outer end, the open outer end secured to the central aperture of the shield portion, the open inner end having a peripheral flange, the open inner end being positionable within the user's mouth.

2. A respirator mask for filtering breathed air for preventing a user from breathing unfiltered air, wherein the user having a face including a mouth and nose, the respirator mask comprising, in combination:

a mask portion dimensioned for covering the mouth of the user, the mask portion including an inner portion, an outer portion, and an air chamber therebetween, the mask portion including a generally circular peripheral edge, the peripheral edge including a top edge, a bottom edge, and opposed side edges, the mask portion including a recessed mouth section on the inner portion thereof, the recessed mouth section including a central aperture in communication with the air chamber, the mask portion including a pair of air vents secured to the outer portion thereof, the pair of air vents each having open inner and outer ends, the open inner ends being in communication with the air chamber; and a mouthpiece portion removably coupled with respect to the mask portion, the mouthpiece portion including a shield portion dimensioned for positioning within the recessed mouth section of the mask portion, the shield portion including a central opening being alignable with the central aperture of the recessed mouth section, the mouthpiece portion including an inner tube having an open inner end and an open outer end, the open outer end secured to the central aperture of the shield portion, the open inner end being positionable within the user's mouth.

3. The respirator mask for filtering breathed air as set forth in claim 2, wherein the mask portion includes an elastic band having opposed ends secured to the opposed side edges thereof for extending around the user's head when the mask portion is positioned on the mouth of the user.

4. The respirator mask for filtering breathed air as set forth in claim 2, wherein the mask portion includes a pair of nose sections extending upwardly from the top edge thereof, the pair of nose sections each including upper ends positionable within the nose of the user, the pair of nose sections each having an air tube positioned therein, the air tubes having open upper and lower ends, the open upper ends being exposed through the upper ends of the nose sections, the open lower ends being in communication with the air chamber.

5. The respirator mask for filtering breathed air as set forth in claim 2, wherein the recessed mouth section includes a plurality of peripherally disposed protrusions extending inwardly therefrom and the shield portion includes a plurality of peripherally disposed apertures therethrough for selectively snap-engaging the peripherally disposed protrusions of the recessed mouth section.

6. The respirator mask for filtering breathed air as set forth in claim 2, wherein the open outer ends of the air vents each have a filter screen disposed therein.

7. The respirator mask for filtering breathed air as set forth in claim 2, wherein the open inner end of the inner tube has a peripheral flange.

* * * * *